United States Patent [19]
Panetta et al.

[11] Patent Number: 5,476,865
[45] Date of Patent: Dec. 19, 1995

[54] METHODS OF INHIBITING BONE LOSS

[75] Inventors: Jill A. Panetta, Zionsville; Masahiko Sato, Carmel, both of Ind.

[73] Assignee: Eli Lilly and Company, Indianapolis, Ind.

[21] Appl. No.: 271,405

[22] Filed: Jul. 6, 1994

[51] Int. Cl.$^6$ ................................................. A61K 31/425
[52] U.S. Cl. ................................................. 514/369; 514/424
[58] Field of Search ................................. 514/369, 424

[56]     References Cited

U.S. PATENT DOCUMENTS

| | | | |
|---|---|---|---|
| 5,158,966 | 10/1992 | Lafferty et al. | 514/369 |
| 5,356,917 | 10/1994 | Panetta | 514/369 |

FOREIGN PATENT DOCUMENTS

| | | |
|---|---|---|
| 0211670/B1 | 2/1987 | European Pat. Off. . |
| 0391644/A2 | 10/1990 | European Pat. Off. . |

OTHER PUBLICATIONS

Christiansen, "Prevention and Treatment of Osteoporosis: A Review of Current Modalities", Bone, 13, 535–539 (1992).
Blair et al., "Isolated Osteoclasts Resorb the Organic and Inorganic Components of Bone," The Journal of Cell Biology, 102, 1164–1172 (Apr. 1986).

*Primary Examiner*—José G. Dees
*Assistant Examiner*—Barbara S. Frazier
*Attorney, Agent, or Firm*—James J. Sales

[57]            ABSTRACT

Rhodanine derivatives are utilized as inhibitors of bone loss/bone resorption and cartilage degradation.

5 Claims, No Drawings

METHODS OF INHIBITING BONE LOSS

BACKGROUND OF THE INVENTION

The present invention relates to new methods for treating diseases in vertebrates characterized by bone loss or cartilage degradation. More particularly, the invention relates to compounds capable of inhibiting the bone resorbing and cartilage degrading activity of osteoclasts (also referred to as chondroclasts). The ability of these compounds to potently and specifically inhibit osteoclast (chondroclast) activity makes them excellent candidates for the treatment of diseases characterized by bone loss or cartilage degradation such as post-menopausal osteoporosis, senile osteoporosis, Cushings' syndrome, gonadal dysgenesis, periarticular erosions in rheumatoid arthritis, osteoarthritis, Paget's disease, osteohalisteresis, osteomalacia, hypercalcemia of malignancy, osteopenia due to bone metastases, periodontal disease and hyperparathyroidism and bone loss or cartilage degradation resulting from hysterectomy, glucocorticoid or steroid treatment or long-term treatment with corticosteroids.

Bone is a dynamic tissue that regenerates throughout the life of vertebrates by turning itself over or remodelling. That is, healthy bone is characterized by a balance between the degradation of bone (bone resorption) and the formation of new bone. Osteoclasts are the differentiated cells responsible for the degradation of old or faulty bone. These cells are responsible for the initiation of the remodelling cycle and their activity triggers the osteoblasts to repair the excavations of osteoclasts by laying down new healthy bone. Unhealthy conditions result when an imbalance develops between osteoclastic and osteoblastic activity. The conditions stated above have the balance tipped towards bone loss such that the amount of bone resorbed is inadequately replaced with new bone, resulting in net bone loss.

One of the most common bone disorders is post-menopausal osteoporosis which affects an estimated 20 to 25 million women in the United States alone. Women after menopause experience an increase in the rate of bone turnover with resulting net loss of bone, as circulating estrogen levels decrease with cessation of ovarian function. The rate of bone turnover differs between bones and is highest in sites enriched with trabecular bone, such as the vertebrae and femoral head. The potential for bone loss at the sites immediately following menopause is 4–5% per year. The resulting decrease in bone mass and enlargement of spaces between bone trabeculae leads to increased fracture risk as the mechanical integrity of bone deteriorates rapidly.

At present in the United States there are 20 million people with detectable vertebral fractures and 250,000 hip fractures per year attributable to osteoporosis. The latter case is associated with a 12% mortality rate within the first two years; 30% of the patients will require nursing home care after the fracture. Therefore, bone disorders are characterized by a noticeable mortality rate, a considerable decrease in the survivor's quality of life and a significant financial burden to families.

Essentially all of the conditions listed above should benefit from treatment with agents that inhibit bone resorption. Osteoclasts are unique in their ability to resorb both the hydroxyapatite mineral and organic matrix of bone. They are similar to the cartilage resorbing cells, previously termed chondroclasts. It is for this reason that potent inhibitors of osteoclastic bone resorption should inhibit the cell-mediated degradation of cartilage observed in rheumatoid arthritis and osteoarthritis.

Attempts to fill this patient need include the therapeutic use of estrogen. Estrogen was shown clearly to arrest the bone loss observed after menopause and limit the progression of osteoporosis, but patient compliance is poor because of estrogen side effects. These side effects include an increase in the risk of uterine cancer and a controversial increase in the risk of breast cancer. Additional side effects include the resumption of menses and mastodynia.

Concerns over these undesirable side effects associated with estrogen replacement therapy have led to the development of alternative inhibitors of bone resorption such as calcitonin and bisphosphonates. Calcitonin has been shown to directly inhibit the resorption activity of mammalian osteoclasts and has been widely prescribed in Italy and Japan, However, calcitonin is expensive and appears to be short-lived in efficacy [Christiansen, *Bone*, 13: S35–S39 (1992)]. That is, osteoclasts are able to escape calcitonin inhibition of resorption by down-regulating calcitonin receptors. Therefore, recent clinical data suggest that chronic treatment with calcitonin is ineffective to arrest the post-menopausal loss of bone.

Alternatively, bisphosphonates are potent inhibitors of bone resorption that may be effective in preventing the bone loss of post menopausal women [Sato et al., *J. Cell. Bio.*, 11: 1713–1723 (1990); Sato et al., *J. Clin. Invest.*, 88:2095–2105 (1991); Fleisch, *Bone* 8(S1):S23–S28 (1990); Watts et al, *N. Engl. J. Med.* 323:73–79 (1990)]. While available in Europe, these compounds have yet to be approved in the U.S for conditions other than Paget's disease. In addition, because these compounds have little effect on cortical, bone and are unusually long lived with an in vivo half life of 10 years or more, concerns have been raised about possible future complications. For these reasons, patients are dissatisfied with the currently available treatments for bone disorders and practitioners are reluctant to prescribe bisphosphonates. Similar dissatisfaction also exists for disorders characterized by cartilage degradation, as mechanisms for these disease states are largely unknown.

SUMMARY OF THE INVENTION

The invention provides a method of inhibiting bone resorption, bone loss, and cartilage degradation in a subject comprising administering to said subject a pharmaceutically effective dose of a compound of the following formula

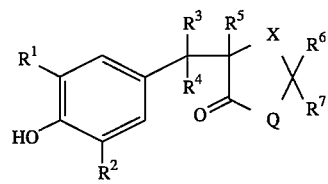

wherein $R^1$ and $R^2$ are independently hydrogen, hydroxy, $C_1$–$C_6$ alkyl, $C_1$–$C_6$ alkoxy, $C_2$–$C_6$ alkenyl, $C_2$–$C_6$ alkynyl, $$(C_1-C_4 \text{ alkyl}) - \overset{O}{\underset{\|}{O}} - C - (C_1-C_4 \text{ alkyl}), \quad \text{or}$$

-continued

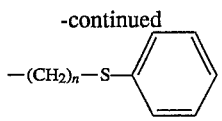

where n is an integer from 0 to 6, inclusive;

$R^3$ is hydrogen or $C_1$–$C_6$ alkyl.

$R^4$ and $R^5$ are hydrogen or when taken together form a bond.

$R^6$ and $R^7$ are independently hydrogen or when taken together from =S or =O, or when one of $R^6$ or $R^7$ is hydrogen, the other is —OH or —SCH$_3$;

X is

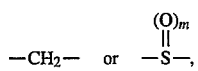

wherein m is 0,1, or 2; and

Q is —CH$_2$—, —O—, or —NR$^8$ where $R^8$ is hydrogen, $C_1$–$C_6$ alkyl, $C_3$–$C_8$ cycloalkyl, $C_2$–$C_6$ alkenyl, —SO$_2$CH$_3$ or —(CH$_2$)$_t$—Y where t is 0,1,2, or 3, and Y is cyano,

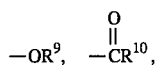

tetrazolyl, —NR$^{11}$R$^{12}$, —SH, —S(C$_1$–C$_4$ alkyl) or

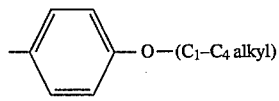

where $R^9$ is hydrogen, $C_1$–$C_4$ alkyl, tosyl, or

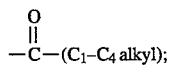

$R^{10}$ is $C_1$–$C_4$ alkyl, $C_1$–$C_4$ alkoxy or —NH$_2$;

$R^{11}$ and $R^{12}$ are independently hydrogen, $C_1$–$C_6$ alkyl, $C_2$–$C_6$ alkenyl, $C_2$–$C_6$ alkynyl, —(CH$_2$)$_n$OH, —(CH$_2$)$_n$—N(C$_1$–C$_4$ alkyl)$_2$, —(CH$_2$)$_n$S(C$_1$–C$_4$ alkyl), or

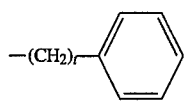

where n is an integer from 0 to 6, inclusive, and t is 0,1,2, or 3; or $R^{11}$ and $R^{12}$ taken together form a morpholinyl, piperidinyl, piperazinyl or an N-methyl piperazinyl ring; and pharmaceutically acceptable salts and solvates thereof.

More particularly, the invention encompasses compounds of the formula

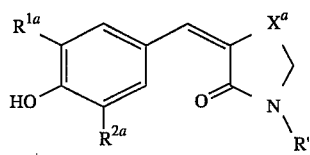

wherein $R^{1a}$ and $R^{2a}$ are independently hydrogen, hydroxy, $C_1$–$C_6$ alkyl, $C_1$–$C_6$ alkoxy,

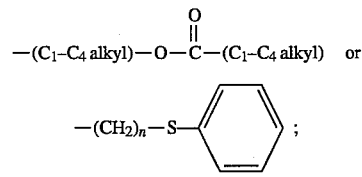

where n is an integer from 0 to 6, inclusive;

R' is hydrogen, methyl, $C_1$–$C_6$ alkyl, or $C_3$–$C_8$ cycloalkyl;

$X^a$ is —CH$_2$— or S; and pharmaceutically acceptable salts and solvates thereof.

DETAILED DESCRIPTION OF THE INVENTION

The current invention concerns the discovery that certain N-methyl thiazolidinones and their analogs are useful in the inhibition of bone loss/resorption and cartilage degradation. The following compounds are encompassed by the invention:

5-[3-ethoxy-4-hydroxy-5-(phenylthio)methylphenyl]methylene-3-methyl-4-thiazolidinone (Compound A)

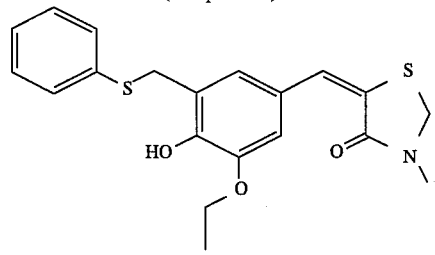

5-[[3-1,1-dimethylethyl]-4-hydroxy-5-isopropylphenyl]methylene]-3-methyl-4-thiazolidinone (Compound B)

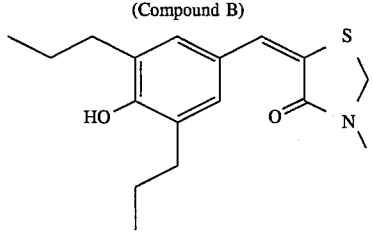

5-[(3,5-dipropyl-4-hydroxyphenyl)methylene]-3-methyl-4-thiazolidinone (Compound C)

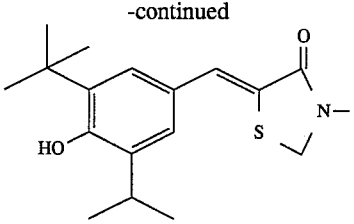

5-3,5-bis(1-methylpropyl)-4-hydroxyhphenyl methylene-3-methyl-4-thiazolidinone (Compound D)

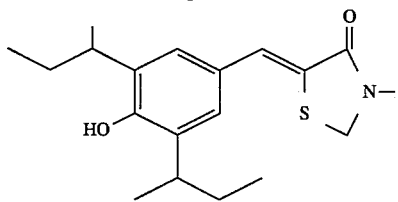

5-[[3,5-bis(1-methylethyl)-4-hydroxyphenyl]methylene]-3-methyl-4-thiazolidinone (Z-isomer)

(Compound E)

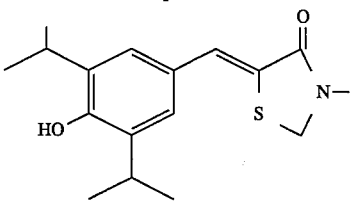

5-[[3-(1,1-dimethylethyl)-4-hydroxy-5-propylphenyl]methylenel-3-methyl-4-thiazolidinone (Compound F)

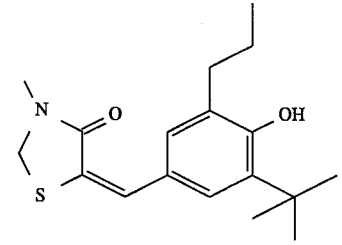

5-[[3,5-bis(1,1-dimethyl)-4-hydroxyphenyl]methylene]-3-methyl-4-thiazolidinone (Compound G)

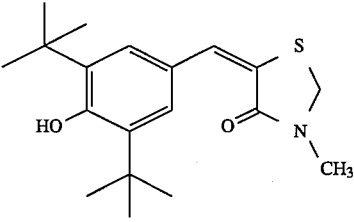

5-[[3-(1,1-dimethylethyl)-4-hydroxy-5-methylphenyl]methylene]-4-thiazolidinone (Compound H)

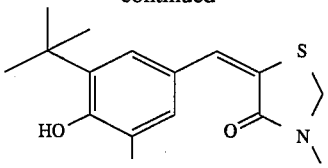

3-[[3,5-bis(1,1-dimethylethyl)-4-hydroxyphenyl]methylene]-1-methyl-2-pyrrolidinone (E-isomer)

(Compound I)

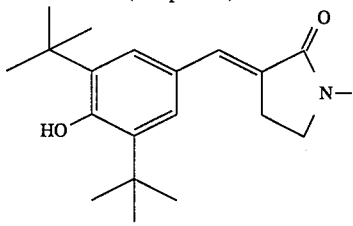

5-[[3,5-bis[3-(acetyloxy)propyl]-4-hydroxyphenyl]-methylene]-3-methyl-4-thiazolidinone (Compound J)

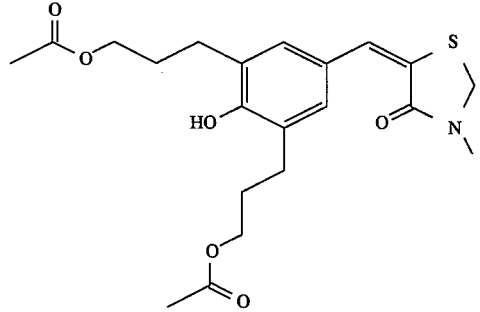

5-[[3,5-bis(1,1-dimethylethyl)-4-hydroxyphenyl]methylene]-3-cyclopropyl-4-thiazolidinone (Compound K)

The compounds employed in the inventive methods may be synthesized by methods well known in the art [U.S. Pat. No. 4,158,966, incorporated herein by reference].

As used herein, a bone loss disease means any disease or condition characterized by a net loss of bone or cartilage. Bone loss diseases include diseases such as post-menopausal osteoporosis, rheumatoid arthritis, osteoarthritis, Paget's disease, Cushing's syndrome, hyperparathyroidism, osteohalisteresis, osteomalacia, hypercalcemia associated with malignancy, osteopenia due to bone metastases, periodontal disease and bone loss occurring as a result of hysterectomy, treatment with glucocorticoids or steroids or long-term treatment with corticosteroids. Inhibit is defined to include its generally accepted meaning which includes retarding, preventing, restraining, slowing or reversing.

For therapeutic treatment of the specified indications, one or more compounds of the disclosed formula may be administered as such, or can be compounded and formulated into pharmaceutical compositions in unit dosage form for parenteral, oral, nasal or intravenous administration or, preferably, transdermal or rectal administration. Such pharmaceutical compositions are prepared in a manner well known in the art and comprise at least one active compound associated with a pharmaceutically acceptable carrier. The term "active compound", as used throughout this specification, refers to at least one compound of the general formula disclosed herein or pharmaceutically acceptable salts thereof.

The compounds are effective over a wide dosage range and, for example, dosages per day Will normally fall within the range from 0.001 to 10 mg/kg, more usually in the range of from 0.01 to 1 mg/kg. However, it will be understood that the effective amount administered will be determined by the physician in light of the relevant circumstances including the condition to be treated, the choice of compound to be administered, and the chosen %route of administration, and therefore the above dosage ranges are not intended to limit the scope of the invention in any way.

In such a composition, the active compound is known as the "active ingredient". In making the compositions, the active ingredient will usually be mixed with a carrier, may be in the form of a capsule, sachet, paper or other container. When the carrier serves as a diluent, it may be a solid, semisolid, or liquid material which acts as a vehicle, excipient, or medium for the active ingredient. Thus, the composition can be in the form of tablets, pills, powders, lozenges, sachets, cachets, elixirs, emulsions, solutions, syrups, suspensions, soft and hard gelatin capsules, sterile injectable solutions and sterile packaged powders.

Some examples of suitable carriers, excipients and diluents include lactose, dextrose, sucrose, sorbitol, mannitol, starches, gum acacia, calcium phosphate alginates, calcium salicate, microcrystalline cellulose, polyvinylpyrrolidone, cellulose, tragacanth, gelatin, syrup, methyl cellulose, methyl-and propylhydroxybenzoates, talc, magnesium stearate, water and mineral oil. The formulations can additionally include lubricating agents, wetting agents emulsifying and suspending agents, preserving agents, sweetening agents or flavoring agents. The compositions may be formulated so as to provide quick, sustained, or deleted release of the active ingredient after administration to the patient by employing procedures well known in the art.

For oral administration, a compound can be admixed with carriers and diluents, molded into tablets, or enclosed in gelatin capsules. The mixtures can alternatively be dissolved in liquids such as 10% aqueous glucose solution, isotonic saline, sterile water or the like and administered intravenously or by injection.

The compositions are preferably formulated in a unit dosage form, each dosage containing from about 0.04 to about 900 mg and, more frequently, from about 1 to about 500 mg of the active ingredient. The term "unit dosage form" refers to physically discreet units suitable a unitary dosages for human subjects and other mammals, each unit containing a predetermined quantity of active material calculated to produce the desired therapeutic effect, in association with the required pharmaceutically acceptable carrier. By "pharmaceutically acceptable", it is meant the carrier, diluent or excipient must be compatible With the other ingredients or the formulation and not deleterious to the recipient thereof.

The following examples are illustrative only and are not intended to limit the scope of the invention in any way. The meaning of the term "active ingredient" is as defined above.

FORMULATION 1

Hard gelatin capsules are prepared using the following ingredients:

|  | Quantity (mg/capsule) |
| --- | --- |
| Active ingredient | 250 |
| Starch, dried | 200 |
| Magnesium stearate | 10 |
| Total | 460 mg |

FORMULATION 2

|  | Quantity (mg/capsule) |
| --- | --- |
| Active ingredient | 250 |
| Cellulose, microcrystalline | 200 |
| Silicon dioxide, fumed | 10 |
| Stearic acid | 5 |
| Total | 665 mg |

The components are blended and compressed to form tablets each weighing 665 mg.

FORMULATION 3

An aerosol solution is prepared containing the following components:

|  | Weight |
| --- | --- |
| Active ingredient | 0.25 |
| Ethanol | 25.75 |
| Propellant 22 (chlorodifluoromethane) | 70.00 |
| Total | 100 |

The active compound is mixed with ethanol and the mixture added to a portion of the Propellant 22, cooled to −30° C. and transferred to a filling device. The required amount is then fed to a stainless steel container and diluted with the remainder of the propellant. The valve units are then fitted to the container.

FORMULATION 4

Tablets, each containing 60 mg of active ingredient are made as follows:

|  | Weight |
| --- | --- |
| Active ingredient | 60 mg |
| Starch | 45 mg |

-continued

|  | Weight |
|---|---|
| Microcrystalline cellulose | 35 mg |
| Polyvinylpyrrolidone (as 10% solution in water) | 4 mg |
| Sodium carboxymethyl starch | 4.5 mg |
| Magnesium stearate | 0.5 mg |
| Talc | 1 mg |
| Total | 150 mg |

The active ingredient, starch and cellulose are passed through a No. 45 mesh U.S. sieve and mixed thoroughly. The aqueous solution containing polyvinyl pyrrolidone is mixed with the resultant powder, and the mixture then is passed through a No. 14 mesh sieve. The granules so produced are dried at 50° C. and passed through a No. 18 mesh U.S. sieve. The sodium carboxymethyl starch, magnesium stearate and talc, previously passed through a No. 60 mesh U.S. sieve, are then added to the granules which, after mixing are compressed in a tablet machine to yield tablets each weighing 150 mg.

FORMULATION 5

Capsules, each containing 80 mg of active ingredient, are made as follows:

|  | Weight |
|---|---|
| Active ingredient | 80 mg |
| Starch | 59 mg |
| Microcrystalline cellulose | 59 mg |
| Magnesium stearate | 2 mg |
| Total | 200 mg |

The active ingredient, cellulose, starch, and magnesium stearate are blended, passed through a No. 45 mesh U.S. sieve, and filled into hard gelatin capsules in 200 mg quantities.

FORMULATION 6

Suppositories, each containing 225 mg of active ingredient, are made as follows:

|  | Weight |
|---|---|
| Active ingredient | 225 mg |
| Saturated fatty acid glycerides | 2,000 mg |
| Total | 2,225 mg |

The active ingredient is passed through a No. 60 mesh U.S. sieve and suspended in the saturated fatty acid glycerides previously melted using the minimum heat necessary. The mixture is then poured into a suppository mold of nominal 2 g capacity and allowed to cool.

FORMULATION 7

Suspensions, each containing 50 mg of active ingredient per 5 mL dose, are made as follows:

|  | Amount |
|---|---|
| Active ingredient(s) | 50 mg |
| Sodium carboxymethyl cellulose | 50 mg |
| Syrup | 1.25 mL |
| Benzoic acid solution | 0.10 mL |
| Flavor | q.v. |
| Color | q.v. |
| Purified water to total | 5 mL |

The active ingredient is passed through a No. 45 mesh U.S. sieve and mixed with the sodium carboxymethyl cellulose and syrup to form a smooth paste. The benzoic acid solution, flavor and color are diluted with a portion of the water and added, with stirring. Sufficient water is then added to produce the required volume.

FORMULATION 8

An intravenous formulation may be prepared as follows:

|  |  |
|---|---|
| Active ingredient | 100 mg |
| Isotonic saline | 1,000 mL |

The N-methyl 4-thiazolidinones and analogs disclosed herein were found to inhibit the in vitro bone resorption activity of hen osteoclasts When assayed as described in Sato et al., *J. Cell Bio.*, 111:1713–1723 (1990). Laying hens (DeKalb XL) maintained on a calcium deficient diet (R5070C-9, Purina Mills, Mo.) for three to six weeks and exposed to 18 hours light/day were sacrificed by carbon dioxide inhalation. Medullary bone was harvested from split femora and tibiae of each bird.

The bone suspension was washed in PBS (phosphate buffered saline) and pressed through a 110 um nylon mesh and incubated in 0.2% NaCl for 3 min. at 37° C. to lyse red blood cells. Cells were collected by centrifugation at 350 g for 5 minutes at 4° C. The collected cells were then sedimented through 70% serum for 90 min. at 4° C. in 50 mL tubes (Fisher Scientific Co., Pittsburgh, Pa.). The bottom 5 mL from the preceding step was layered onto a discontinuous Nycodenz gradient, (Accurate Chemical & Scientific Corp., Westbury, N.Y.) with steps of 1.073, 1.09 and 1.143 g/cm$^3$. The gradients so prepared were spun at 350 g for 20 minutes at 4° C. The monocyte band was collected, washed in PBS and cultured overnight at 39.5° C. in complete alpha MEM without phenol and containing 10% charcoal filtered chicken serum and 10% charcoal filtered fetal calf serum. Attached cells were then collected and replated at 3×10$^5$ cells/cm$^2$ in alpha MEM plus 10% serum and cytosine-1-B-D arabinofuranoside (Sigma Chemical Co., St. Louis, Mo.) into 48 well plates (Costar Data Packaging Corp.) with or without test compounds. After four days, plated cells were washed 3X in complete alpha MEM media and then incubated for an additional 3 days with 100 ug of 20–53 um particles of crushed rat bone radiolabeled in vivo with [$^3$H]proline [Blair et al. *J. Cell Bio.* 102:1164–1172 (1986)] and a control or one of the compounds disclosed herein at a concentration of 1 uM. Resorption activity was quantitated by measuring the [$^3$H] released into the media at day 6 from bone particles. In Table I, data are presented as mass of bone resorbed (ug) between days 4–7, and with repsect to controls without added compound, as percent control.

TABLE I

| Compound | Mass of bone resorbed (ug) | Percent Control |
| --- | --- | --- |
| A | 7.52 ± 44 | 25.24 ± 1.46 |
| B | 0.6 ± .45 | 1.9 ± 1.45 |
| C | 5.36 ± 0.63 | 18 ± 2.13 |
| D | 2.3 ± 0.2 | 6.95 ± 0.6 |
| E | 2.97 ± 0.5 | 5.47 ± 0.09 |
| F | 2.91 ± 0.021 | 5.78 ± 0.42 |
| G | 10.47 ± 1.28 | 24.98 ± 3.06 |
| H | 7.55 ± 1.31 | 25.54 ± 4.43 |
| I | 11.97 ± 2.99 | 36.24 ± 9.06 |
| J | 9.18 ± 0.32 | 37.67 ± 1.32 |
| K | 15.66 ± 0.43 | 54.43 ± 1.49 |

Bone Slice Assay

Compounds E and G also inhibited bone resorption in isolated osteoclasts. This model was shown to be integral to a mechanistic understanding of another class of resorption inhibitors, bisphosphonates. [Fleisch, *Bone* 8 (S1):S23–S28 (1990); Sato et al., *J. Bone Min. Res.* 5:31–40 (1990); Sato et al. *J. Clin. Invest.* 88:2095–2105 (1991)]. Bisphosphonates, and in particular amino hydroxybutylidene bisphosphonate, were shown to be therapeutically efficacious in treating Paget's disease [Pedrazzoni et al., *Bone Miner.* 7:301–307 (1989); O'Doherty et al., *J. Bone. Miner. Res.,* 5:483–491 (1990)]; hypercalcemia of malignancy [Ralston, et al., *Lancet ii:* 1180–1182 (1989); Bilezikian, *N. Engl. J. Med.* 326:1196–1203 (1992)]; osteolytic lesions due to metastases [Attardo-Parrinello et al., *Arch. Intern. Med.* 147:1629–1633 (1987)]; steroid and glucocorticoid induced osteoporosis [Reid et al., *Lancet i:*143–146 (1988); Reid et al., *J. Bone Miner. Res.* 5:619–623 (1990)]; and postmenopausal osteoporosis [Watts et al, *N. Engl. J. Med.* 323:73–79 (1990)]. The ability of Compounds E and G to inhibit osteoclast activity supports the conclusion that these compounds and their analogs, like the bisphosphonates, have therapeutic utility in vivo in the treatment of bone disorders.

The resorption assay with human osteoclasomas was conducted as a modified version of that described in Sato and Grasser, *J. Bone Miner. Res.* 5:31–40 (1990). Bone disks, 5.4 mm diameter and 0.15 mm thick were cut in cross section from the diaphysis of steer femora. These disks were rehydrated in 0.075 mL medium 199 (Gibco, N.Y.) pH 7 in 96 well plates (Costar, Mass).

Discarded giant cell tumors (osteoclastoma tissue) were obtained at the time of definitive surgical treatment. All patients had at least one previous biopsy to confirm this diagnosis. At the time of explantation, the tumor tissue was immediately placed in complete medium 199 (Gibco, N.Y.) with 20% charcoal stripped heat inactivated fetal calf serum at room temperature and mechanically disaggregated with scalpels. After gently pipetting 60X with a wide bore pipette, the cell suspension was passed through a 110 um mesh (Spectrum, Los Angeles, Calif.). Osteoclastoma suspensions (0.15 mL/well) were aliquoted into the bone slice containing wells at a density of 100–400/bone slice. 0.10 mL of one of the test compounds (each at a concentration of 1 uM) Or control was then added to yield a total volume of 0.25 mL/well. After incubation for 2 days at 37° C., bone slices were devitalized in distilled $H_2O$, fixed in 3% formaldehyde, dehydrated through 5–95% ethanol and stained with 1% toluidine in 1% sodium borate for 40 seconds.

Resorption activity was quantitated by reflected polarized light microscopy (RLM), described in Sato and Grasser, *J. Bone Miner. Res.* 5:31–40 (1990). In this method, a fluorescence microscope (Microphot, Nikon) was adapted for reflected light microscopy by inserting a ¼ plate between crossed polarizers in the epi mode. Fluorescence objectives of long working distance with adjustable correction collars (10X, 20X, Nikon) were fitted with rotatable ¼ plates (Polaroid Corp. Mass.) mounted as the front element. Correction collars were necessary for 20X objectives and higher to correct for the presence of the ¼ plate and the absence of a coverslip. Coverslips were not used in order to eliminate stray reflections below the ¼ plate. Immersion oil (Nikon) was added between the objective front lens and the ¼ plate to minimize reflections at this interface. Oil was not placed between objective and specimen.

The surfaces of the bone slices were scanned for resorption lacunae by rotating the ¼ plate 0°–45° with respect to the plane of polarization in Hg-vapor illumination. Quantitation of resorbed areas of bone slices examined by RLM was achieved through digital image processing of video images (Newvicon, Dage-MTI, Inc., Michigan City, Ind.).

Table II details the resorption activity observed for controls without added compound, and the effect of Compounds E and G on the number and density of resorption lacunae per bone slice. Data are also presented in terms of resorption as a percentage of the control.

TABLE II

| Compound | Resorption | Percent Control |
| --- | --- | --- |
| Control | 134 ± 29 | 100 |
| E (1 uM) | 17 ± 3.7 | 4.97 ± 3.37 |
| G (1 uM) | 59 ± 12.8 | 30.88 ± 16.49 |

We claim:

1. A method of inhibiting bone resorption in a subject comprising administering to said subject a pharmaceutically effective dose of a compound of the structure

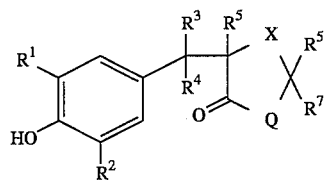

wherein $R^1$ and $R^2$ are independently hydrogen, hydroxy, $C_1$–$C_6$ alkyl, $C_1$–$C_6$ alkoxy, $C_2$–$C_6$ alkenyl, $C_2$–$C_6$ alkynyl,

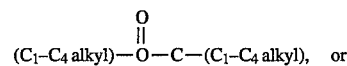

($C_1$–$C_4$ alkyl)—O—C(=O)—($C_1$–$C_4$ alkyl), or

-continued

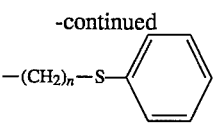

where n is an integer from 0 to 6, inclusive;

$R^3$ is hydrogen or $C_1$-$C_6$ alkyl $R^4$ and $R^5$ are hydrogen or when taken together form a bond $R^6$ and $R^7$ are independently hydrogen or when taken together from =S or =O, or when one of $R^6$ or $R^7$ is hydrogen, the other is —OH or —$SCH_3$;

X is

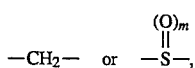

wherein m is 0,1, or 2; and

Q is —$CH_2$—, —O—, or —$NR^8$ where $R^8$ is hydrogen, $C_1$-$C_6$ alkyl, $C_3$-$C_8$ cycloalkyl, $C_2$-$C_6$ alkenyl, —$SO_2CH_3$ or —$(CH_2)_t$—Y where t is 0,1,2, or 3, and Y is cyano,

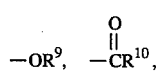

tetrazolyl, —$NR^{11}R^{12}$, —SH, —S($C_1$-$C_4$ alkyl) or

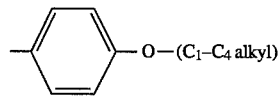

where $R^9$ is hydrogen, $C_1$-$C_4$ alkyl, tosyl, or

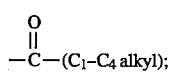

$R^{10}$ is $C_1$-$C_4$ alkyl, $C_1$-$C_4$ alkoxy or —$NH_2$;

$R^{11}$ and $R^{12}$ are independently hydrogen, $C_1$-$C_6$ alkyl, $C_2$-$C_6$ alkenyl, $C_2$-$C_6$ alkynyl, —$(CH_2)_n$OH, —$(CH_2)_n$—N($C_1$-$C_4$ alkyl)$_2$, —$(CH_2)_n$S($C_1$-$C_4$ alkyl), or

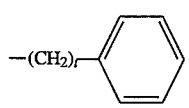

where n is an integer from 0 to 6, inclusive, and t is 0,1,2, or 3; or $R^{11}$ and $R^{12}$ taken together form a morpholinyl, piperidinyl, piperazinyl or an N-methyl piperazinyl ring; and pharmaceutically acceptable salts and solvates thereof.

2. A method of inhibiting bone resorption in a subject comprising administering to said subject a pharmaceutically effective dose of a compound of the structure

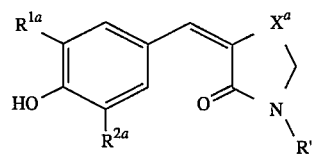

wherein $R^{1a}$ and $R^{2a}$ are independently hydrogen, hydroxy, $C_1$-$C_6$ alkyl, $C_1$-$C_6$ alkoxy,

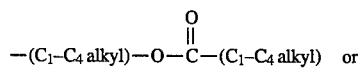

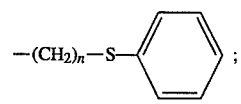

where n is an integer from 0 to 6, inclusive;

R' is hydrogen, methyl, $C_1$-$C_6$ alkyl, or $C_3$-$C_8$ cycloalkyl;

$X^a$ is —$CH_2$— or S; and pharmaceutically acceptable salts and solvates thereof.

3. The method of claim 1 wherein the compound is selected from the group consisting of

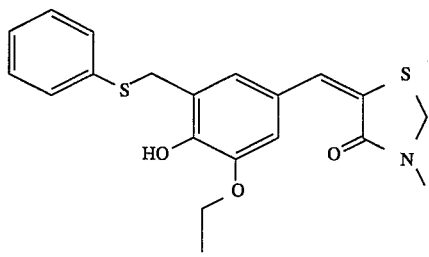

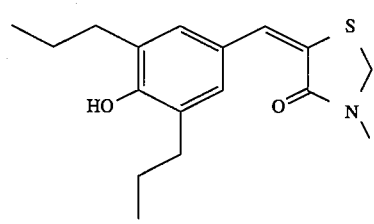

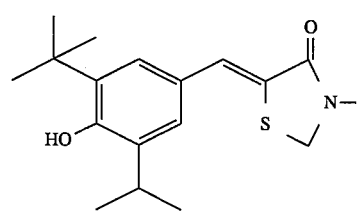

-continued
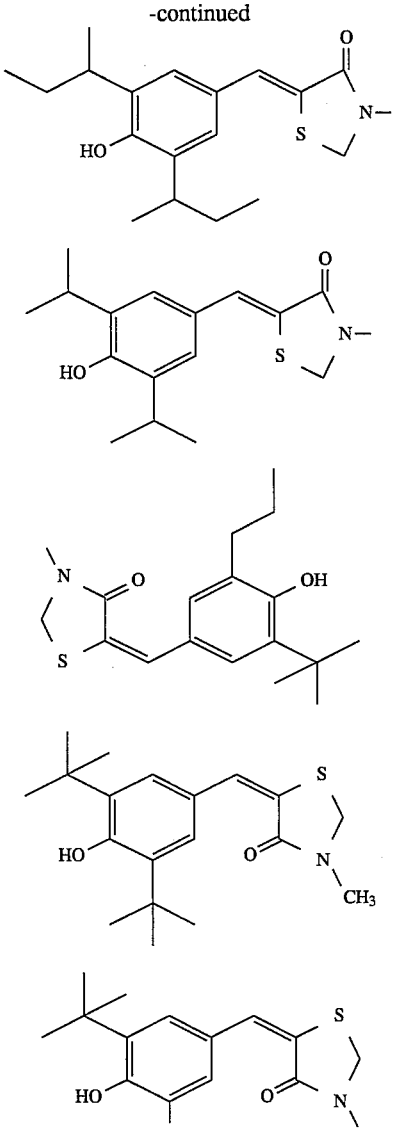
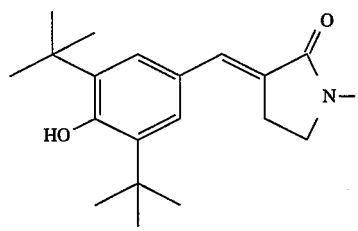
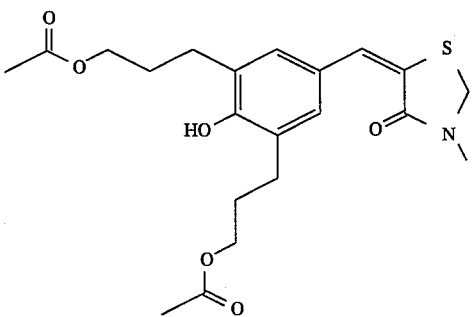
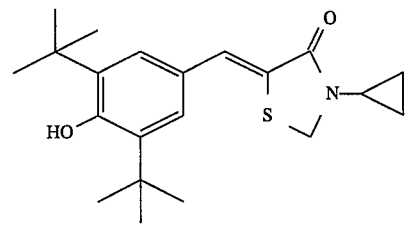
and pharmaceutically acceptable salts and solvates thereof.
4. The method of claim 2 wherein said subject has or is susceptible to osteoporosis.
5. The method of claim 2 wherein the compound is administered prophylactically.
* * * * *